(12) United States Patent
Garudadri

(10) Patent No.: US 12,336,792 B2
(45) Date of Patent: *Jun. 24, 2025

(54) EXTRACTING SENSOR SIGNALS FROM A COMPOSITE SIGNAL

(71) Applicant: Harinath Garudadri, La Jolla, CA (US)

(72) Inventor: Harinath Garudadri, La Jolla, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/100,628

(22) Filed: Jan. 24, 2023

(65) Prior Publication Data

US 2023/0157556 A1 May 25, 2023

Related U.S. Application Data

(63) Continuation of application No. 17/001,358, filed on Aug. 24, 2020, now Pat. No. 11,583,192, which is a
(Continued)

(51) Int. Cl.
*A61B 5/021* (2006.01)
*A61B 5/00* (2006.01)
(Continued)

(52) U.S. Cl.
CPC ............ *A61B 5/02141* (2013.01); *A61B 5/01* (2013.01); *A61B 5/087* (2013.01); *A61B 5/11* (2013.01);
(Continued)

(58) Field of Classification Search
CPC ....... A61B 5/02141; A61B 5/01; A61B 5/087; A61B 5/11; A61B 5/14552; A61B 5/318;
(Continued)

(56) References Cited

U.S. PATENT DOCUMENTS

| 5,339,824 A | 8/1994 | Engira |
| 5,661,651 A | 8/1997 | Geschke et al. |

(Continued)

FOREIGN PATENT DOCUMENTS

| BE | 1019968 A3 | 3/2013 |
| CN | 103118203 A | 5/2013 |

(Continued)

OTHER PUBLICATIONS

Haykin and Moher, Communication Systems, Mar. 2009, Wiley, 5th Edition, Chapter 2, ISBN: 978-0-471-69790-9 (Year: 2009).*

*Primary Examiner* — Jonathan T Kuo
(74) *Attorney, Agent, or Firm* — Total Awareness Consulting Services; Robert Winslow

(57) ABSTRACT

A second device comprises at least one ADC. The ADC(s) are configured to receive a composite analog signal. The composite analog signal comprises a plurality of modulated signals. Each signal in the modulated signals has been modulated to a distinct center frequency. Each signal in the modulated signals has originated from a sensor. At least two of the signals in the modulated signals comprise a plurality of frequency components. The ADC(s) are configured to convert the modulated signals into a digital signal. The second device comprises at least one control unit. The control unit(s) are configured to receive the digital signal. The control unit(s) are configured to perform: band pass filtering, frequency demodulation, and extraction of the signals sensed by the sensors.

20 Claims, 10 Drawing Sheets

Related U.S. Application Data continuation of application No. 14/499,345, filed on Sep. 29, 2014, now Pat. No. 10,758,132.

(60) Provisional application No. 61/909,440, filed on Nov. 27, 2013.

(51) Int. Cl.
| | | |
|---|---|---|
| *A61B 5/01* | (2006.01) | |
| *A61B 5/087* | (2006.01) | |
| *A61B 5/11* | (2006.01) | |
| *A61B 5/1455* | (2006.01) | |
| *A61B 5/318* | (2021.01) | |
| *A61B 5/369* | (2021.01) | |
| *H04M 1/72409* | (2021.01) | |

(52) U.S. Cl.
CPC .......... *A61B 5/14552* (2013.01); *A61B 5/318* (2021.01); *A61B 5/369* (2021.01); *A61B 5/746* (2013.01); *H04M 1/72409* (2021.01); *A61B 5/6898* (2013.01); *A61B 2560/0214* (2013.01); *A61B 2560/045* (2013.01); *A61B 2562/227* (2013.01); *H04M 1/724094* (2022.02)

(58) Field of Classification Search
CPC ....... A61B 5/369; A61B 5/746; A61B 5/6898; A61B 2560/0214; A61B 2560/045; A61B 2562/227; H04M 1/72409; H04M 1/724094

See application file for complete search history.

(56) References Cited

U.S. PATENT DOCUMENTS

| | | | |
|---|---|---|---|
| 5,735,285 A | 4/1998 | Albert et al. | |
| 7,914,468 B2 | 3/2011 | Shalon et al. | |
| 8,052,600 B2 | 11/2011 | Beck et al. | |
| 8,509,882 B2 | 8/2013 | Albert et al. | |
| 10,758,132 B2* | 9/2020 | Garudadri | A61B 5/746 |
| 11,583,192 B2* | 2/2023 | Garudadri | A61B 5/02141 |
| 2002/0111556 A1 | 8/2002 | Wegner | |
| 2003/0163052 A1 | 8/2003 | Mott et al. | |
| 2004/0220487 A1* | 11/2004 | Vyshedskiy | A61B 7/04 |
| | | | 600/528 |
| 2004/0220488 A1 | 11/2004 | Vyshedskiy et al. | |
| 2007/0030116 A1 | 2/2007 | Feher | |
| 2008/0284599 A1 | 11/2008 | Zdeblick et al. | |
| 2009/0171170 A1 | 7/2009 | Li et al. | |
| 2010/0033303 A1* | 2/2010 | Dugan | G01P 15/02 |
| | | | 340/5.82 |
| 2012/0156933 A1* | 6/2012 | Kreger | A61B 5/14552 |
| | | | 439/625 |
| 2013/0034237 A1 | 2/2013 | Olafsson et al. | |
| 2013/0331663 A1 | 12/2013 | Albert et al. | |

FOREIGN PATENT DOCUMENTS

| | | |
|---|---|---|
| CN | 103315721 A | 9/2013 |
| WO | 2012/155245 A1 | 11/2012 |

* cited by examiner

EXTRACTING SENSOR SIGNALS FROM A COMPOSITE SIGNAL

TECHNICAL FIELD

The disclosure relates to physiology monitoring devices and more particularly relates to an accessory device for sensing and providing physiological signals to another ambulatory device for monitoring and interpreting physiology of a person.

BACKGROUND AND PRIOR ART

Recent advances in mobile computing and energy-efficient communication have shown promise in the continuous acquisition, storage, and processing of physiological signals. Pervasive sensors deployed in next generation networks have enabled algorithms capable of efficient and accurate information processing. The monitoring of physiology of a person including, but not limited to electrocardiogram (ECG or EKG) signals and Electroencephalography (EEG) signals may be performed with electronic devices which are used very regularly by any person.

The monitoring of the ECG signals are performed by interpretation of the electrical activity of a heart over a period of time, as detected by electrodes attached to surface of the skin and recorded by a device external to a body of a person. The recording produced by electrical activity of heart is termed as an ECG. The monitoring of EEG signals is performed by recording and interpretation of electrical activity along the scalp of a person. The EEG measures voltage fluctuations resulting from ionic current flows within the neurons of the brain.

Known in the art are methods for measuring physiological signals of a person such as breathing, body temperature, oxygen saturation and blood pressure. For monitoring breathing of a person, a spirometer may be used. A spirometer is an instrument that measures air flow while breathing and estimates the air capacity of the lungs, for diagnosing asthma or Chronic Obstructive Pulmonary Disease (COPD). The body temperature is an important indication of health including fever, sepsis, heat rash, or any other disease which may affect the persons. Measurement of temperature may be carried out using an electronic device with an Infra Red (IR) sensor.

Pulse oximeters may be used to monitor Oxygen saturation in a person, which is measurement of concentration of oxygen in arterial blood reaching tissues. The peripheral oxygen saturation (SpO2) can be measured non-invasively by using a pulse oximeter. A pulse oximeter device comprises a photodetector that responds to red and infra-red light through tissue, such as finger tip, ear lobe, etc. and then processes the signal to estimate SpO2. Arterial Blood Pressure (BP) is another physiological signal that can be estimated non-invasively, using many techniques including the oscillometric principle. The amplitude of pressure change in a cuff on the upper arm of a person, which is inflated and then deflated, is sensed by a pressure sensor. The sensed signal is processed to estimate systolic and dialostic BP. For measuring any physiological parameter, plurality of sensors are used to sense some specific aspect of underlying physiology. The sensed signals are then processed using software algorithms running on special purpose medical devices, general purpose computers, microprocessors, ASICs, or any other computing device.

Recently, cellphones, smartphones, tablets and other personal devices have become ubiquitous. These devices along with laptops and desktop computers are herein after referred as a Host device. Most of the host devices provide a headphones socket that provides audio signal to the ear buds. Also, they provide power to microphone and receive the signal from the microphone. Headphones that incorporate microphones for telecommunications are typically called headsets. Hereinafter in this description, the terms headphone and headset are used interchangeably. A headphone jack and a headphone socket require a physical, electrical connection to interoperate. Hereinafter in this description, the terms jack and socket are used to represent any electrical connection. The wiring for headphones and headsets using typical 3.5 mm, 4 pin jacks and compatible sockets is known as TRRS (tip, ring, ring, and sleeve) configuration as shown below.

| Pin Number | Pin Name | Description |
| --- | --- | --- |
| 1 | Tip | Left Audio Out |
| 2 | Ring 1 | Right Audio Out |
| 3 | Ring 2 | Common/Ground |
| 4 | Sleeve | Microphone Input |

Known in the art is a headphone or electret microphones cable with a headphone jack on one side, which may be interfaced with the Host device. The headphones commonly used in hands free, voice call applications require microphone-bias to power a preamplifier that is internal to the microphone assembly. The socket on a host device or mobile device or consumer device provides the bias on the Microphone input (pin-4) and Common/Ground (pin-3), while receiving the audio signal from the microphone on the same two pins. The essential point is that power to a sensor and signal communication from the sensor is accomplished on a two-wire interface. A limitation of this AC-coupled architecture is that the input signals can only be AC signals, without having any information in the lower frequencies of the input signals such as audio and speech.

FIG. 1 shows a typical microphone connection to headphone socket on Smartphones and Tablets. The junction gate field-effect transistor (JFET) provides amplification and impedance matching. The resistor R values are in the rage of 1-10 KΩ, which provides the required bias voltage and sources current for JFET operation. Also, the capacitor C values are in the range of 1-50 µF and blocks DC voltage while passing audio signals for ADC. The microphone becomes a current source, delivering few hundred µA. Thus, the two-wire interface can provide power to the sensor and also receive the analog data from the sensor using ac-coupled interface.

FIG. 2 shows a conventional ECG Equivalent Circuit. The impedance of the circuit of FIG. 2 for the commonly used electrodes is shown in FIG. 3. The impedance can be sometimes as high as 500 kΩ. This variability is due to the variation in off the shelf Ag/AgCl electrodes and due to aging in disposable electrodes. The ECG signals have a bandwidth in the range of 0.05 to 100 Hz. Typical amplitude of ECG signals is about 5 mV. The signals can sometimes ride on a DC bias of ±300 mV. There is significant diagnostic information in the lower frequencies that would be filtered by the high pass filtering action at the audio socket in smartphones. The reusable sintered Ag/AgCl electrodes mitigate the electrode variability to a large extent. Similarly, for signals such as air flow, temperature, light intensity, and pressure which correspond to certain physiological aspects of interest to clinicians, the frequency content is well below that of speech and audio. As the capacitor C in FIG. 1, will block low frequency signals, such a socket is not useful for receiving physiological signals.

In a patent application US 20130331663 discloses heart monitoring system usable with a smartphone or computer. It discloses a personal monitoring system with a sensor assembly to sense physiological signals. The system requires frequency modulated (FM) physiological audio signal and requires a carrier frequency to be in the range of 6-20 kHz. Here, the FM signal is an audio signal and is not an electric signal. Also, the audio transmitter of the personal monitoring system transmits an audio signal to the microphone.

A U.S. Pat. No. 8,509,882 discloses a personal monitoring device usable with a smartphone or computer. The device uses a frequency modulation (FM) demodulation and generates acoustic signal. The carrier signal is in the range of 6-20 kHz. The device uses an in-built microphone and an audio isolation transformer to interface to smartphone or a computer.

Typically, for headphones, powering the microphone sensor using microphone bias provided by the electronic device is known. The microphone sensor is limited to sensing speech, audio and ambient sound signals. The audio jack interface of the electronic device is not used for ECG, EEG and other physiological signals. Systems for powering devices connected to the audio jack and provide digital communication with the phone are known in the art. In these systems, the phone generates an audio signal that is rectified and filtered to generate power for an external device. The microphone port is reserved for communicating discrete data from the device to the phone. The microphone bias is not used to power external devices.

Accordingly, a need exists for a device and method for monitoring physiological signals using cellphones, smartphones, tablets and other personal devices.

SUMMARY

The shortcomings of the prior art are overcome and additional advantages are provided through the provision of a method and system as described in the description.

One embodiment of the present disclosure is a first device also referred as a smart accessory or a smart cable. The first device is having at least one instrumentation block and a jack connectable to a second device with a socket and at least one sensor. The first device comprising at least one amplifier in the instrumentation block configured to amplify at least one signal received from the at least one sensor and one or more modulators in the instrumentation block. The one or more modulators are configured to modulate at least one amplified signal. The at least one modulated signal is transmitted to the second device upon connecting the jack to the socket. The analog signal from the first device is referred to as "composite analog signal". The signal transmitted from the first device is understood to be composite analog signal, even if not explicitly stated for brevity. Also, the first device is configured to receive power from the second device upon connecting the jack to the socket. The at least one signal is one of electrocardiogram (ECG), Electroencephalography (EEG), motion, airflow of respiratory system, body temperature, light intensity of arterial oxygen saturation level, blood pressure and any other physiology signal.

Another embodiment of the present disclosure is a second device also referred as host device having at least one ADC, at least one control unit, at least one modem and at least one socket connectable to a first device with at least one instrumentation block and a jack. The second device comprising the at least one ADC configured to receive an analog signal from the first device through the at least one socket upon connecting to the jack and convert the analog signal in to a digital signal. The analog signal received by the second device is understood to be composite analog signal, even if not explicitly stated for brevity. The control unit configured to receive the digital signal and perform band pass filtering, demodulation and extracting features from at least one raw signal sensed by the first device.

Yet another embodiment of the present disclosure is a first device with at least one sensor, at least one actuator, an instrumentation block and a jack connectable to a second device with a socket. The first device comprises at least one amplifier in the instrumentation block configured to amplify at least one signal received from at the least one sensor. Also, the first device comprises at least one driver unit in the instrumentation block to actuate at least one actuator, wherein the at least one driver receives a driver signal from the second device upon connecting the jack to the socket. The at least one composite analog signal sensed by the at least one sensor is transmitted to the second device upon connecting the jack to the socket.

Another embodiment of the present disclosure is a second device with at least one ADC, at least one DAC, at least one control unit, at least one modem and at least one socket connectable to a first device with at least one instrumentation block and a jack. The second device comprises the at least one ADC configured to receive a composite analog signal from the first device through the at least one socket upon connecting to the jack and convert the analog signal in to a digital signal. The at least one control unit is configured to provide at least one actuation signal to the at least one DAC, receive at least one digital signal from the at least one ADC and process the at least one digital signal received from the at least one ADC. The at least one drive signal is transmitted from the at least one DAC to the first device upon connecting the at least one socket to the jack.

Another embodiment of the present disclosure is a method for processing at least one signal being sensed by at least one sensor using a first device. The method comprising receiving the at least one signal being sensed by the at least one sensor, amplifying the received at least one signal, performing a predefined modulation on the amplified at least one signal and transmitting the composite signal with at least one modulated signal to a second device through a jack of the first device, upon connecting the jack to at least one socket of the second device.

Yet another embodiment of the present disclosure is a system to acquire and process at least one signal from at least one sensor. The system comprises a first device with at least one instrumentation block and a jack connectable to a second device with a socket and the at least one sensor. The first device comprises at least one amplifier in the instrumentation block configured to amplify at least one signal received from the at least one sensor and one or more modulators in the instrumentation block, wherein each of the one or more modulators configured to modulate at least one amplified signal, the composite signal with at least one modulated amplified signal is transmitted to the second device upon connecting the jack to the socket. The system also comprises a second device with at least one ADC, at least one control unit, at least one modem and at least one socket connectable to the first device. The second device comprising the ADC configured to receive the composite signal with at least one modulated amplified signal from the first device through the at least one socket upon connecting to the jack and convert the modulated amplified signal in to a digital signal and the control unit configured to receive the digital signal and perform band pass filtering, demodulation and extracting at least one raw signal sensed by the at least one sensor.

Another embodiment of the present disclosure is a method for processing sensor signals. The method comprises receiving one or more signals sensed by one or more sensors, amplifying the received one or more sensed signals, performing a predefined modulation on the one or more amplified signals, combining the one or more modulated signals to form a composite analog signal, and transmitting the composite signal to a host device for further processing.

Yet another embodiment of the present disclosure is a method for acquiring and processing a composite signal on a second device. The method comprises receiving a composite signal, converting to digital domain, separating one or more signals from the composite signal, demodulating the separated one or more signals to base band, extracting one or more features from the base band signal and optionally communicating the one or more base band signals and the extracted features.

Yet another embodiment of the present disclosure is a third device, which is also a host device, comprising at least one control unit, at least one modem, and at least one Graphical User Interface unit. The at least one control unit is configured to receive at least one digital signal corresponding to the composite analog signal generated by a first device and perform at least one of band pass filtering, demodulation and extracting at least one raw signal sensed by a first device. The third device further comprises one or more band pass filters to perform band pass filtering.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF DRAWINGS

The novel features and characteristics of the disclosure are set forth in the appended claims. The embodiments of the disclosure itself, however, as well as a preferred mode of use, further objectives and advantages thereof, will best be understood by reference to the following detailed description of an illustrative embodiment when read in conjunction with the accompanying drawings. One or more embodiments are now described, by way of example only, with reference to the accompanying drawings in which:

Figure 1:
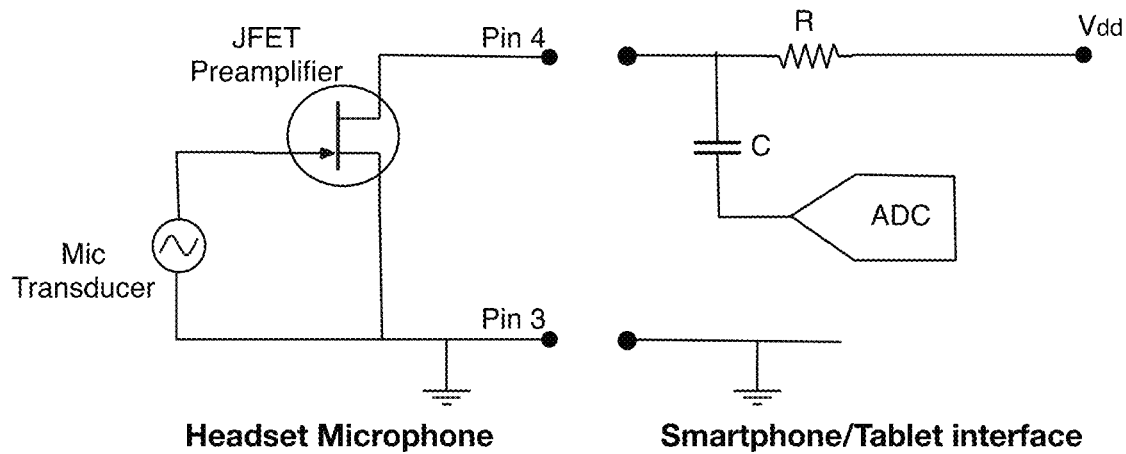
FIG. 1 shows a schematic diagram of a microphone jack and headphone socket, in accordance with a prior art embodiment.
Figure 2:
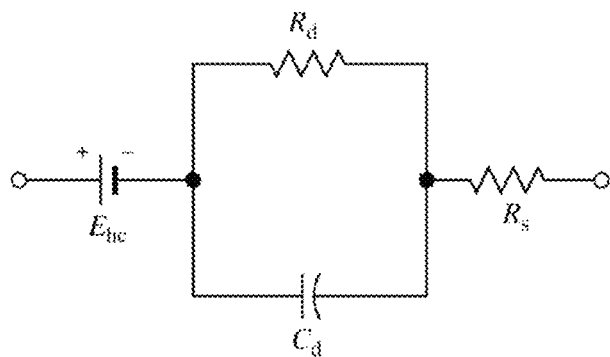
FIG. 2 shows an equivalent circuit for a biopotential sensor, in accordance with a prior art embodiment.
Figure 3:
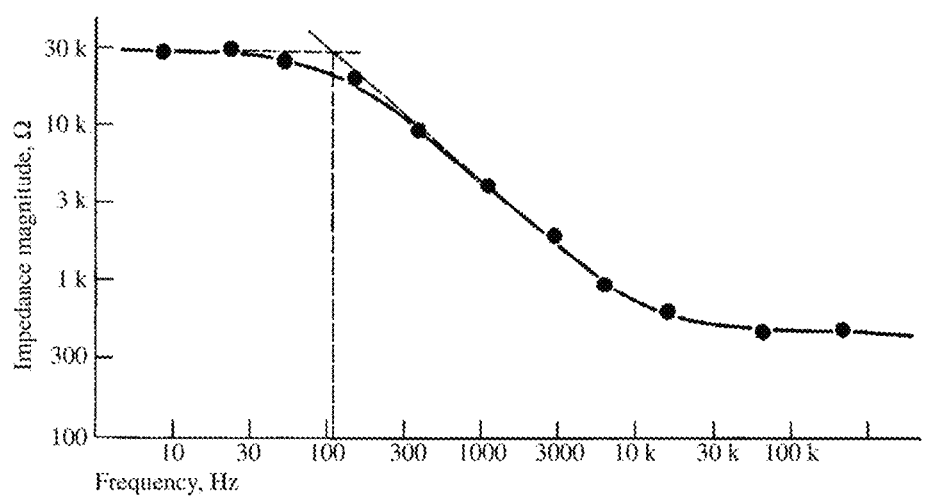
FIG. 3 shows a plot illustrating magnitude of impedance as function of frequency for typical biopotential electrodes, in accordance with a prior art embodiment.

The drawings for the sake of uniformity depict embodiments of the disclosure for purposes of illustration only. One skilled in the art will readily recognize from the following description that alternative embodiments of the structures and methods illustrated herein may be employed without departing from the principles of the disclosure described herein.

DETAILED DESCRIPTION

In the present document, the word "exemplary" is used herein to mean "serving as an example, instance, or illustration." Any embodiment or implementation of the present subject matter described herein as "exemplary" is not necessarily to be construed as preferred or advantageous over other embodiments.

While the disclosure is susceptible to various modifications and alternative forms, specific embodiment thereof has been shown by way of example in the drawings and will be described in detail below. It should be understood, however that it is not intended to limit the disclosure to the particular forms disclosed, but on the contrary, the disclosure is to cover all modifications, equivalents, and alternatives falling within the spirit and the scope of the disclosure.

The terms "comprises", "comprising", or any other variations thereof, are intended to cover a non-exclusive inclusion, such that a setup, device or method that comprises a list of components or steps does not include only those components or steps but may include other components or steps not expressly listed or inherent to such setup or device or method. In other words, one or more elements in a system or apparatus proceeded by "comprises . . . a" does not, without more constraints, preclude the existence of other elements or additional elements in the system or apparatus.

The present disclosure discloses acquiring and processing physiological signals through one or more sensors. The physiological signals include, but are not limited to, Electrocardiography (ECG), Electroencephalography (EEG), motion, airflow of respiratory system, body temperature, arterial oxygen saturation level, and blood pressure, collectively called "Signals" on handheld devices or computing devices such as but not limited to smartphones, tablets, Personal Computers (PCs), etc., collectively called "Host device" or a second device or a third device, using a smart accessory or smartcable or a first device.

One embodiment of the present disclosure is a device also referred to as a first device or smart accessory or a smartcable comprising a jack for connecting the first device to a host device, also referred to as a second device through a socket. Also, the first device comprises an instrumentation block connected with a jack on one side and one or more sensor cables on the other side, wherein the instrumentation block receives predefined signals being sensed by one or more sensors through the one or more sensor cables. The instrumentation block comprises an amplifier to amplify the sensed signals being received from one or more sensors. The amplifier is an instrumentation amplifier. Also, the instrumentation block comprises one or more modulators to perform a predefined modulation on the amplified sensed signals being received from the amplifier. The modulation includes, but not limited to amplitude modulation (AM), phase modulation (PM), frequency modulation (FM), etc. In one embodiment, the predefined modulation is FM and the modulator is a Voltage Controlled Oscillator (VCO). The modulation retains low frequency contents of the amplified sensed signals for further processing. The instrumentation block may comprise a primary and/or a secondary cell for powering the instrument block. Further, the instrumentation block may comprise a regulator to provide predetermined power to the amplifier and the modulator, where said regulator receives power through a jack from a socket of the host device that the smartcable connects to. The modulated signals from the modulator are transmitted as a composite analog signal to the second device for processing through the jack of the first device. The signals being sensed by the one or more sensors are one of ECG, EEG, motion, airflow of respiratory system, body temperature, light intensity changes due to arterial oxygen saturation levels, blood pressure and any other physiological signals.

Figure 4:
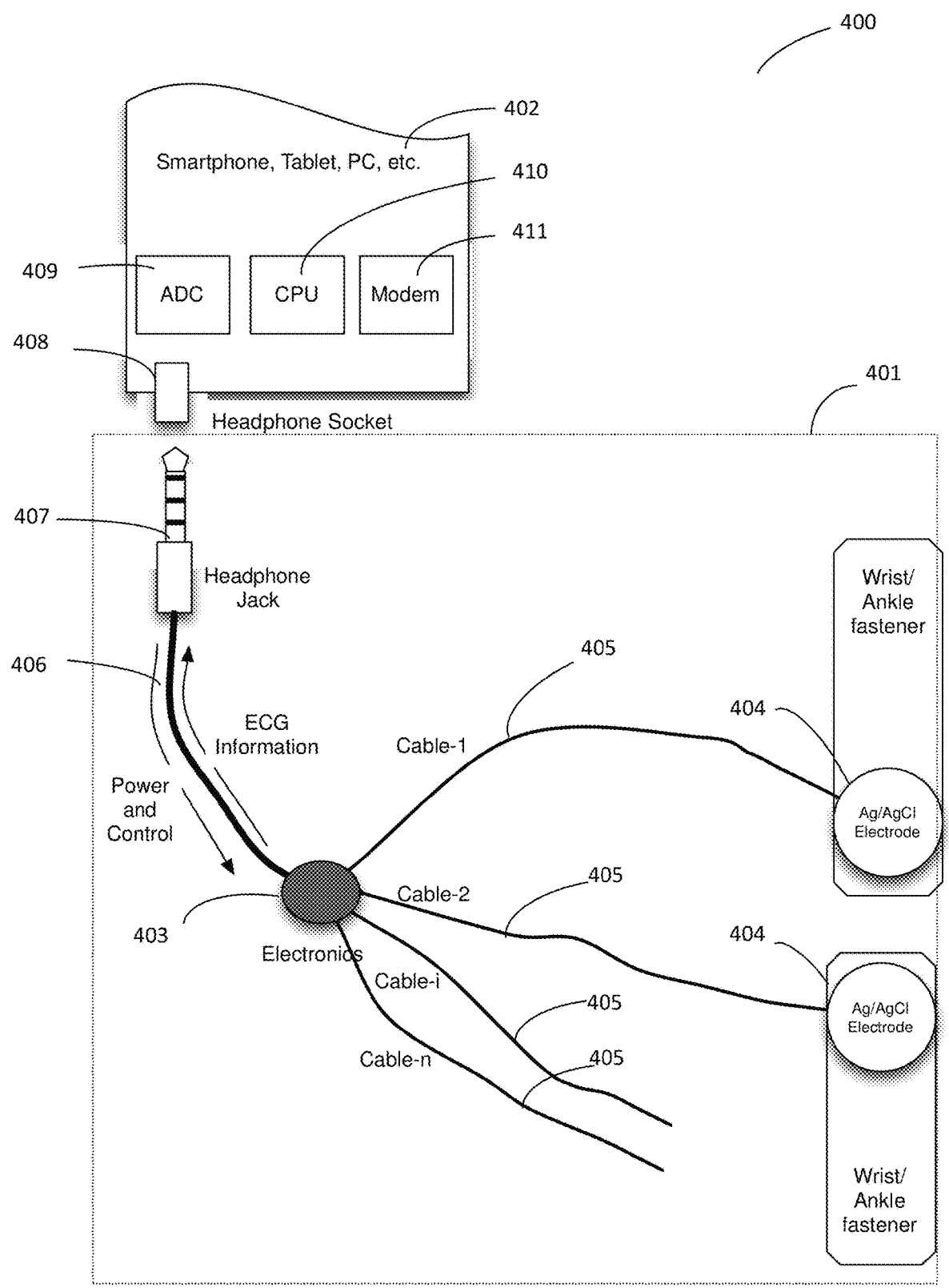
FIG. 4 shows a smart accessory or a smartcable device for acquiring ECG signals on host devices, in accordance with an embodiment of the present disclosure.

An exemplary embodiment of the present disclosure is a cable also referred as smartcable or smart accessory or first device 401, which is shown in FIG. 4. The first device 401 comprises a jack 407 for connection to a host device, referred as a second device 402. The Electronics module or instrumentation block 403 is embedded in the first device 401 and draws power from a headphone socket, referred as a socket 408 to power its operation. The Electronics module 403 further processes signals such as, but not limited to, Electrocardiography (ECG), Electroencephalography (EEG), motion, airflow, temperature, light intensity, pressure, and transmits this information as a composite analog signal to the Host device or the second device 402 via the jack 407 and the socket 408. The Host device 402 may additionally control certain aspects of the electronics module 403 for acquiring and processing plurality of signals. In an exemplary embodiment, the electronics module 403 in the first device connects to one or more transducers/sensors, such as ECG electrodes, collectively referred by a number 404 as shown in FIG. 4 and through cables Cable-1, Cable-2, Cable-i and Cable-n collectively referred by a number 405, as shown in FIG. 4. The transducers at the other end of these cables may include a sintered Ag/AgCl electrode 404 each, embedded in a comfortable ankle/wrist fastener. The sintered Ag/AgCl electrodes 404 provide superior performance for sensing bio potential signals such as EEG and ECG signals. The transducers may include but not limited to other sensors, such as pressure, temperature, motion, airflow, temperature, light intensity, pressure, etc., connected to Cable-1 through Cable-n (these transducers are not shown in FIG. 4).

Figure 10:
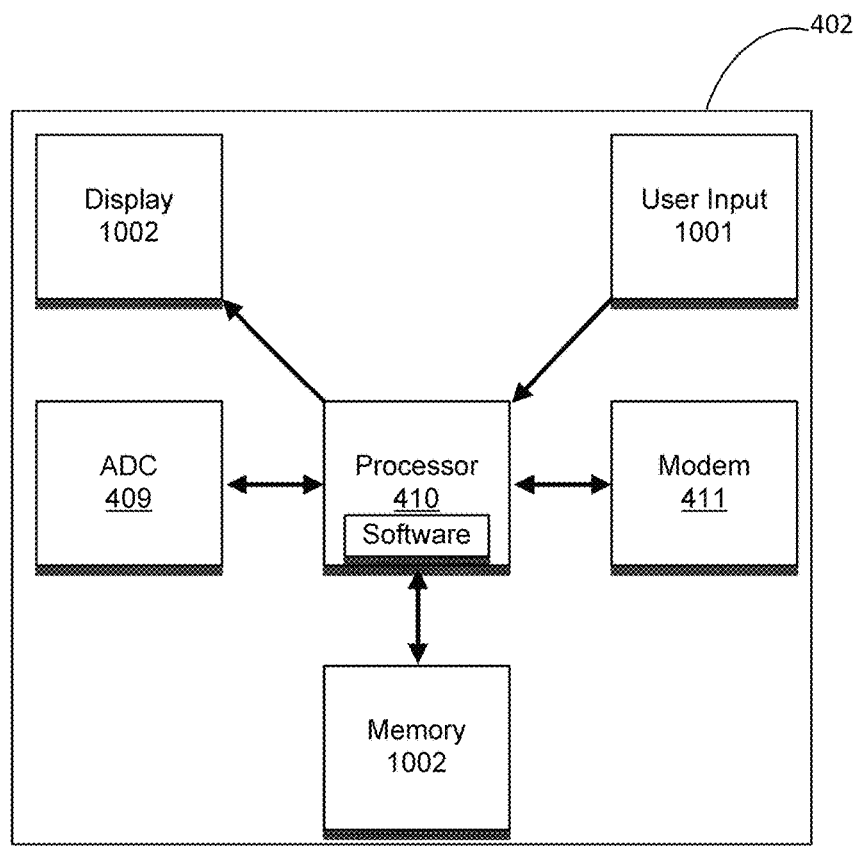
FIG. 10 shows a block diagram of a host device, according to an embodiment of the present disclosure.

In one embodiment, the Host device or the second device 402 comprises an internal Analog-to-Digital Convertor (ADC) 409, a central processing unit (CPU) or referred to as a control unit or a controller 410, memory (not shown in the figure) and a modem 411 to transmit information on any network (not shown in figure), as depicted in FIG. 10. The ADC 409 converts the composite analog signal received from the first device 401 though the socket 408 in to discrete domain. The Host device 402 CPU 410 processes the discrete domain information to extract at least one signal, such as ECG, EEG, motion, airflow, temperature, light intensity, pressure, and any other physiology signals. The Host device 402 may deduce additional information such as, but not limited to the information relevant for convalescence, health monitoring, fitness, endurance training, etc. from the plurality of extracted raw signals. The Host device 402 may communicate at least one of extracted signals and the deduced information through the modem 411 via wired or wireless communication to another device also referred to as third device such as but not limited to, clinician devices, coach devices. The Host device 402 may also communicate said information to any network or the Internet via access points, gateways, etc. In one embodiment, the Host device 402 may digitize the composite analog signal and transmit it to a third device for further processing.

Figure 9:
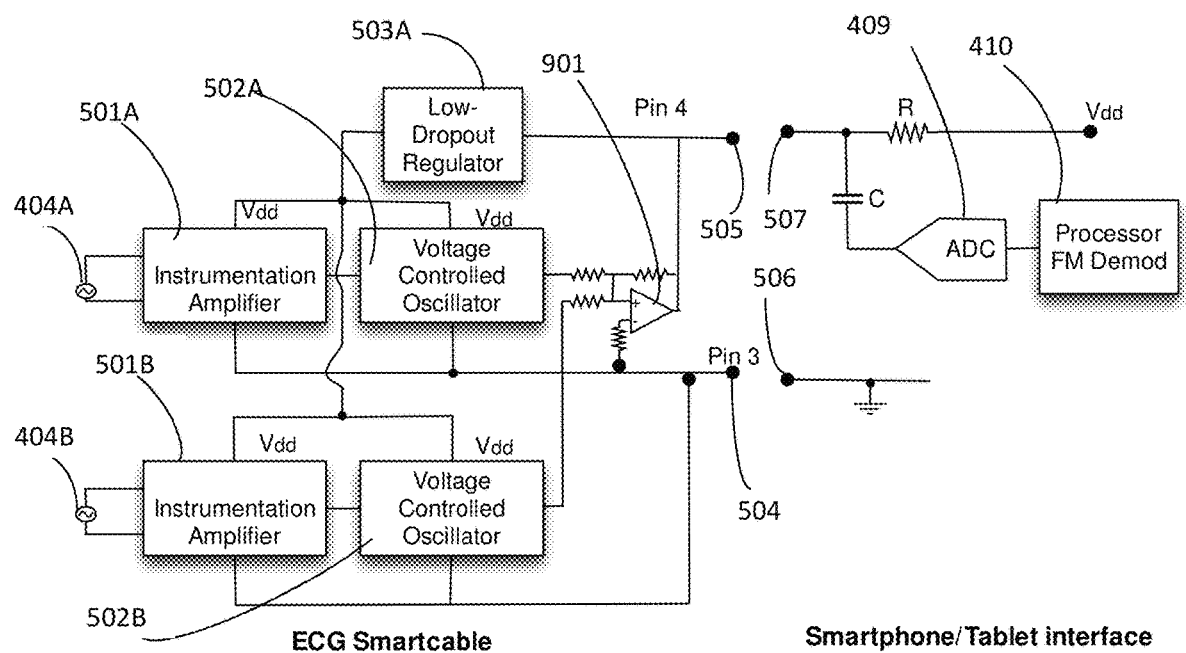
FIG. 9 shows a smart accessory or smartcable for multiple physiological parameters according to an alternative embodiment of the present disclosure.

As shown in FIG. 4, the transducers/sensors which sense the signals include, but are not limited to, ECG and EEG, motion, airflow, temperature, light intensity, pressure, and any other physiology signals which have very low frequency content that are clinically relevant. The headphone socket 408 of a typical Host device 402 is AC coupled, since there is no audio information below 20 Hz. The instrumentation/electronics module 403 pre-conditions the signal and performs frequency modulation (FM) to the audio band in the range of, for example, 20-20000 Hz. For a first device or smart accessory or a smartcable 401 supporting plurality of sensors 404A, 404B, etc. as shown in FIG. 9, each sensor signal is modulated to a different center frequency, thus enabling a pair of wires connected to Pin 4 505 and Pin 3 504 to carry a plurality of sensor signals. The modulation may be FM, although other types of analog modulation techniques such as AM, PM, etc. that shift the spectrum of the sensor signal are also possible. The present disclosure enables mobile devices such as, but not limited to, smart phones and tablets which are becoming ubiquitous to acquire and process the ECG, EEG, motion, airflow, temperature, light intensity, pressure, and other sensor signals using a smartcable system, thus extending their use as ambulatory diagnostic instruments. The battery and processing power of the Host device 402 is leveraged to lower the cost, while providing superior signal quality commensurate with diagnostic instruments used inside hospital walls.

In one embodiment, the first device 401 may obtain sensor signals from sensors incorporated in other wearable devices such as, but not limited to vests and helmets that provide adequate real estate to house ADC, processing and transmission, including a battery to power the electronics. However, the number of wires or cables 405 required to connect all the sensors 404 to the electronics module 403 may be prohibitive from space, reliability and cost perspectives. As an example, in one embodiment, EEG caps may include electrodes in the range of 64 to 256. Also, there may be motion related signals generated by the sensors that provide additional information. In one embodiment, the vests may comprise few tens of ECG's and other sensors. In such applications, a two wire system may be used to carry a composite analog signal multiple sensor signals, wherein each sensor signal is modulated to a different center frequency. The wearable system can use much higher spectrum than the audio band of 20 to 20,000 Hz, since the composite analog signal will interface to an ADC that is not limited by the audio band headphone interface. In one embodiment, such a wearable system may use separate lines for powering the electronics and a two-wire interface for the signal plane to communicate the composite analog signal to the electronics module. In another embodiment, such a wearable system may incorporate a primary or a secondary cell to power the electronics in the said first device.

Figure 5A:
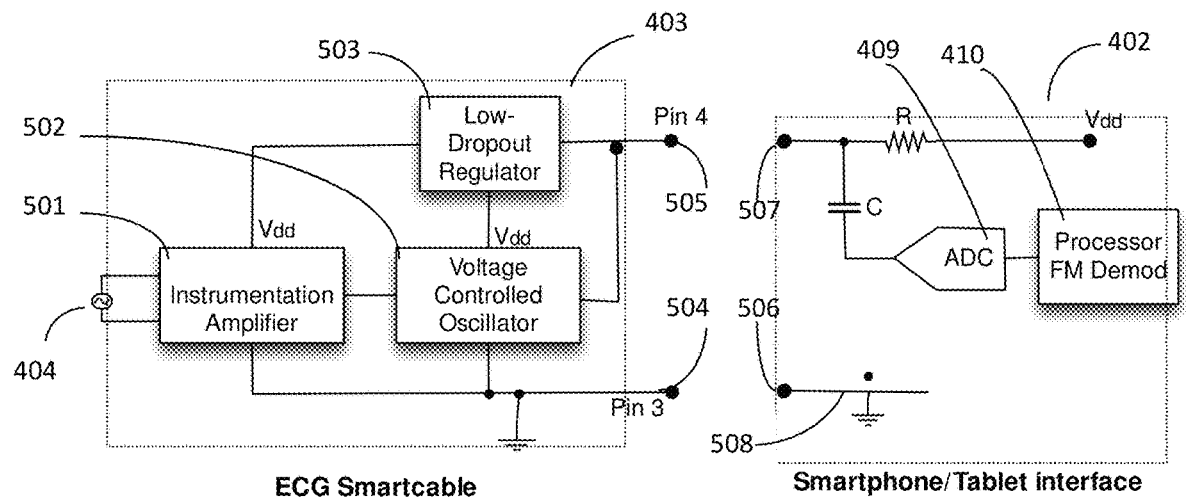
FIG. 5A shows a block diagram of the electronic module or instrumentation unit of a smartcable, according to an embodiment of the present disclosure.

FIG. 5A shows a block diagram 400 of the system including the electronic module or instrumentation unit 403 of a smartcable or a first device 401, and block diagram of a second device 402 in accordance with an embodiment of the present disclosure. As shown in the FIG. 5A, the instrumentation unit 403 comprises an instrumentation amplifier (IA) 501, at least one low dropout regulator (LDO) 503 and one or more modulators or modulator circuits or voltage controlled oscillators (VCO) 502. The IA 501 receives signals from one or more sensors/transducers through one or more cables. The signals may include, but not limited to ECG, EEG, airflow, temperature, light intensity, pressure and motion signals. The differential signal from two cables (or one ECG Lead), connected to two sensors/transducers is converted to a single-ended signal and amplified by the IA. In one embodiment, there may be multiple IA's 501 in an electronic module 403 of a first device 401. To preserve low frequency information in the signal, a frequency modulation is used to heterodyne the signal to audio band using the VCO 502. The IA 501 and the VCO 502 are powered using the microphone-bias from Pin 4 505. A capacitor (not shown in FIG. 5A) may be placed in close proximity to the power supply pins of the IA 501 and the VCO 502 to improve Power Supply Rejection Ration (PSRR). Alternately, a Low-dropout (LDO) regulator 503 can be used to provide stable power to the first device 401 electronics assembly.

The second device or host device 402 comprises an ADC 409 to digitise the composite analog signal from the first device 401 in to a composite discrete signal. Further, the second device 402 comprises a processor with a bandpass filter for filtering the composite discrete signal to extract at least one modulated signal. Further, the second device may comprise a software or a demodulation module 410 to extract raw baseband signals such as, but not limited to, ECG, EEG, motion, airflow, temperature, light intensity, pressure, and other physiological signals from the said discrete signals. A very high FM bandwidth, for example about 5-6 kHz, centered around 5-10 kHz, may be used to provide a high resolution signal after demodulation. This will result in a very low Input Referred Noise (IRN), for example less than 10 µV, after demodulation. An IRN of less than 10 µV is typically specified for high-end ECG monitoring instruments used during cardiac procedures in hospitals. The FM bandwidth may be different for other signals such as motion, airflow, temperature, light intensity, pressure, etc., depending on the maximum frequency (i.e. ½ Nyquist frequency) of the said signal.

One embodiment of the present disclosure is an ECG Sensor Interface. The notations RA, LA, LL and RL are normally used to represent electrodes placed on the subject's Right Arm, Left Arm, Left Leg and Right Leg, respectively. An ECG lead/cable is the differential signal provided between two electrodes. The ECG limb leads are the differential signals between two ECG electrodes placed on the subject's limbs. Lead I corresponds to LA-RA, Lead II corresponds to LL-RA and Lead III corresponds to LL-LA. The electrode placed on the right leg (RL) is used to place a modified version of the sensed signals back on the patient, in order to reduce the effects of power line interference and improve Common Mode Rejection Ratio (CMRR). This approach is called Right Leg Drive (RLD). The RLD is very useful in ECG systems powered from main lines.

In one embodiment of the present disclosure, an Instrumentation Amplifier (IA) 501 of a first device 401 is capable of acquiring any sensed signals such as, but not limited to ECG signals from limb leads. As shown in FIG. 5A, a differential input interface is provided to the IA 501. For example, the IA 501 used may be IC AD8232. The AD8232 provides for many ECG sensing functions in an integrated circuit, reducing the need for multiple discrete components.

Figure 5B:
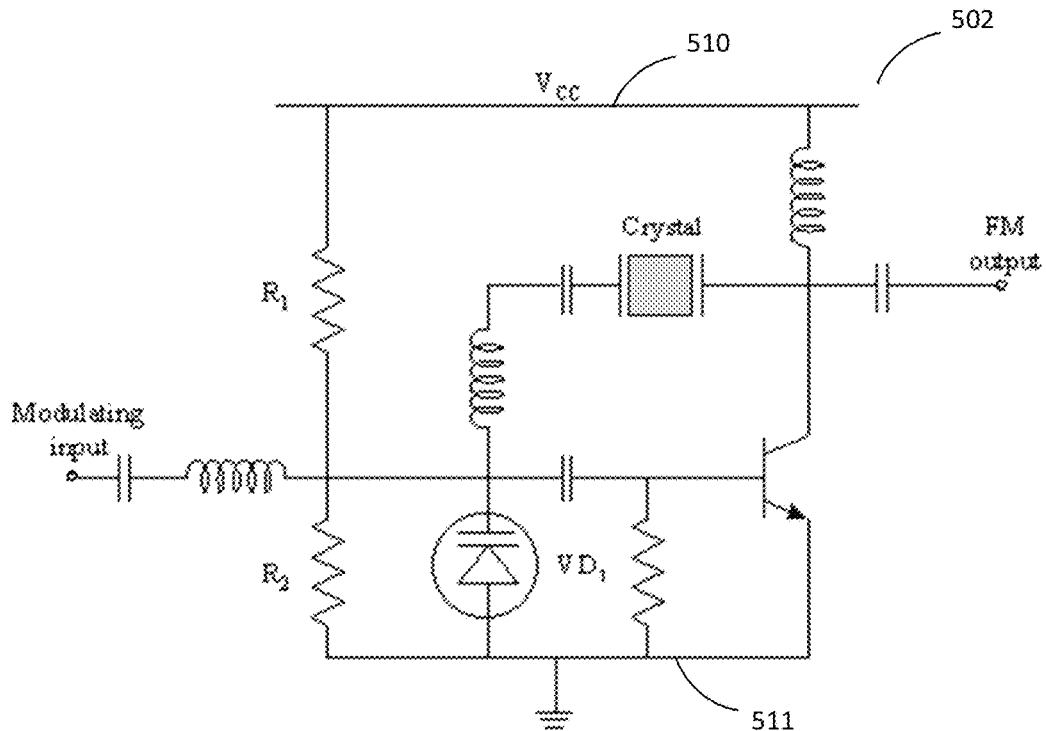
FIG. 5B shows a conventional modulator circuit.

The one or more Modulators or Voltage Controlled Oscillator (VCO) 502 of the electronic module 403 as shown in FIG. 5A may be realized using multiple configurations for operation in the audio band. The VCO 502 of the electronic module 403 functions as a frequency modulator. An example of a VCO is a Wein Bridge Oscillator. In another example, the VCO 502 is a varactor diode $VD_1$ shown in FIG. 5B. The FIG. 5B illustrates an example modulator circuit of the many modulation circuits known in the art. The output of the IA 501 drives the modulating input of the VCO 502 shown in FIG. 5B. The Vcc line 510 as shown in FIG. 5B is same as Vdd line 507 in the FIG. 5A.

Electrophysiological signals or bio-potential signals such as EEG and EEG may be sensed using electrodes but for parameters such as, but not limited to, motion, airflow, temperature, light intensity and pressure, they are first converted in to electrical signals using an appropriate sensors.

Figure 6A:
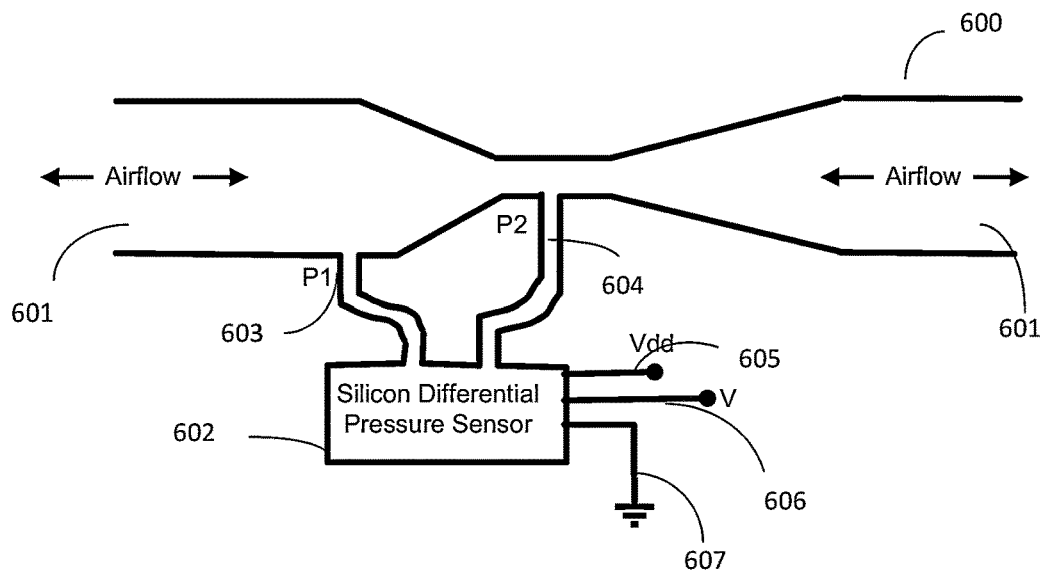
FIG. 6A shows an airflow sensor based on venturi principle with 3-Terminal interface, according to known art.

An airflow sensor using a venturi tube 600 with 3-Terminal interface is shown in FIG. 6A. The constriction in the venturi tube 600 creates a differential pressure between P1 603 and P2 604 shown in FIG. 6A. A silicon differential pressure sensor 602 converts the pressure difference due to airflow in the veturi tube in to an electrical signal. The differential pressure sensor comprises a three wire interface consisting of ground 607, power supply Vdd 605 and signal V 606. The signal V 606 is a spirometry signal which has amplitudes that correspond to breathing volumes and frequency corresponding to the breathing rate. The venturi tube 600 is shown as an example and other transducers for sensing airflow are known in the art. The spirometry signal includes both positive and negative swings corresponding to exhalation and inhalation; however the frequency content is very low.

Figure 6B:
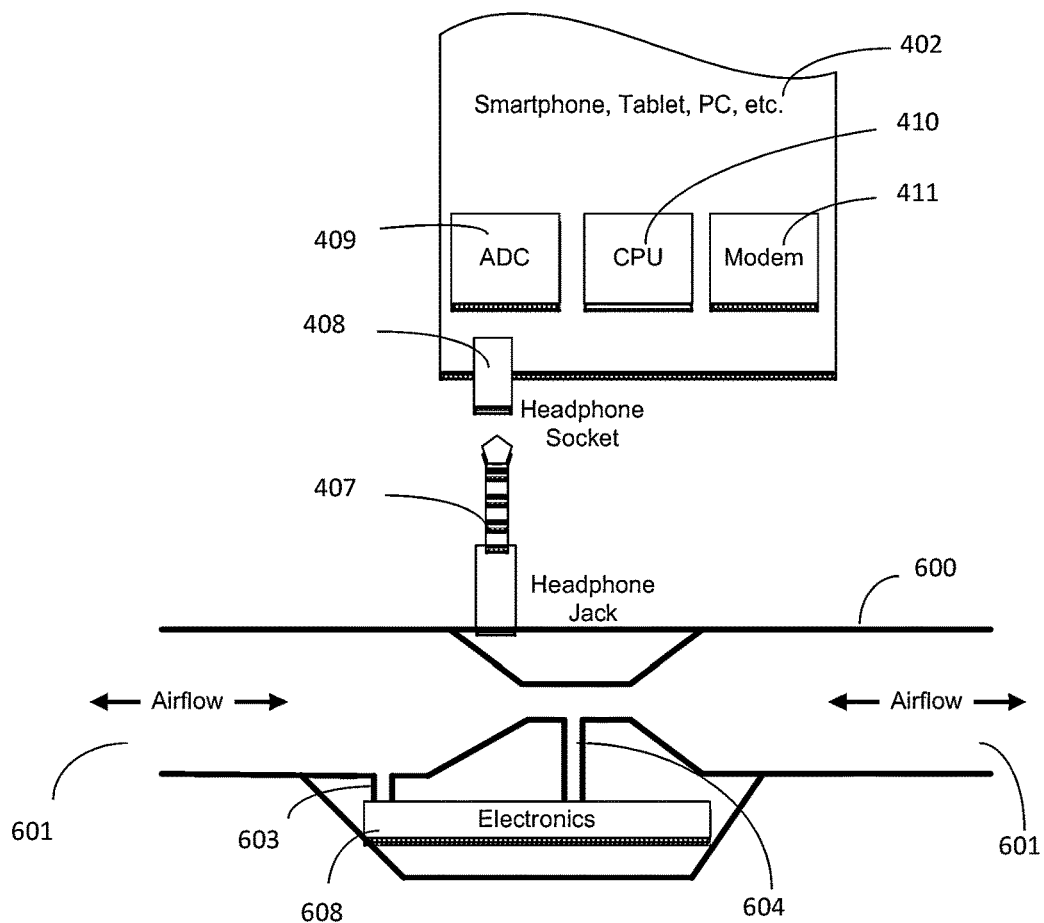
FIG. 6B shows smart accessory for acquiring breathing signals on host devices, according to another embodiment of the present disclosure.
Figure 7A:
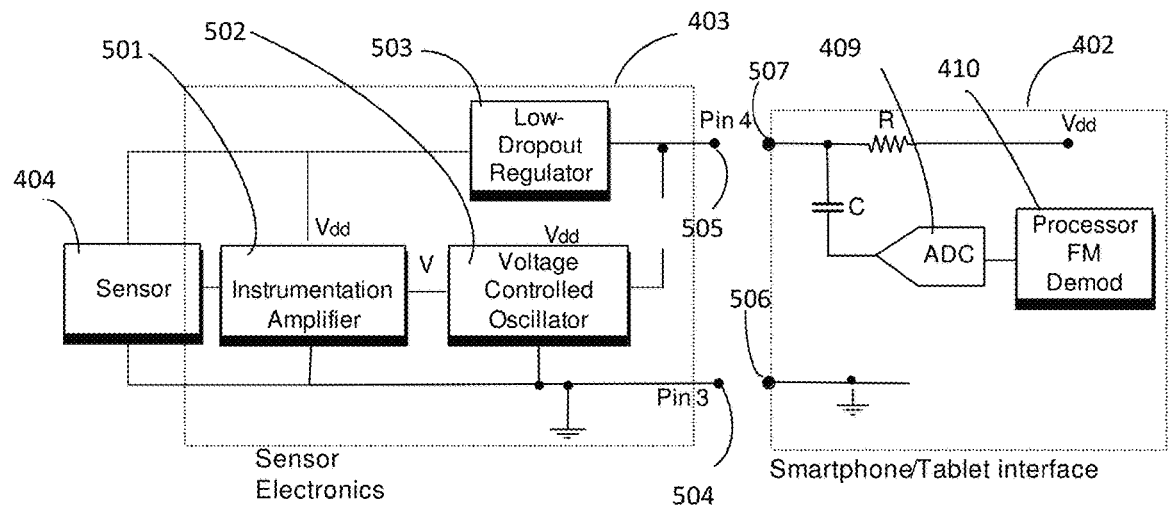
FIG. 7A shows a block diagram of an electronic module of the smart accessory or smartcable, according to an embodiment of the present disclosure.

In one embodiment of the present disclosure, the sensor may be an airflow sensor, provisioned in a first device connected to a second device for performing pulmonary function tests (PFTs) and for measuring physiological parameters of lung function. In order to preserve the low frequency information in the spirometry signal, a frequency modulation technique is used to heterodyne the spirometry signal to audio band using modulator circuit or voltage controlled oscillator (VCO), which is in the electronics module 608, as shown in FIG. 6B. FIG. 7A shows a block diagram of the electronic module or instrumentation unit of the first device, in accordance with an embodiment of the present disclosure. As shown in FIG. 7A, the IA 501 and the VCO 502 are powered using a microphone-bias from a Pin 4 505 from the second device upon connecting jack of the first device to a socket of the second device. In one embodiment, the sensor 404 and the electronics 403 may be incorporated in breathing tube 600 equipped with a jack 407 (not shown in the figure) for plugging in to socket of a second device. In another embodiment, the first device or the smartcable may be of negligible length, so that the jack 407 is mounted on the breathing tube 600, as shown in FIG. 6B. In another embodiment of the present disclosure is a primary cell or a secondary cell (figure not shown) may be used in the first device to power to the sensor 404, amplifier 501 and the modulator or VCO 502.

In one example embodiment of the present disclosure, the sensor as shown in FIG. 7A is a Gauge pressure sensor. The gauge pressure sensor comprises one port (not shown in the figure) to measure pressure relative to the atmospheric pressure. The gauge pressure sensor and the associated electronics may be incorporated in an inflatable compression cuff placed on a user's upper arm and a cable with a jack for plugging in to a host device socket (figure not shown). When the cuff is inflated above the systolic pressure and the cuff is deflated, the output signal of the gauge pressure sensor reflects systolic blood pressure (BP), diastolic BP and the Mean Arterial Pressure (MAP). Processing of the pressure sensor signal is performed by oscillometric principles to obtain systolic BP, diastolic BP and MAP values.

The gauge pressure sensor comprises a three wire interface consisting of ground, power supply Vdd and the signal V. The signal V may be referred as oscillometric signal having a frequency components related to heart rate, as the pulsatile flow of blood affects the sensor signal during deflation. In order to preserve the low frequency information in the oscillometric signal, a frequency modulation is used to heterodyne the oscillometric signal to audio band using the VCO, as shown in FIG. 7A. The IA and the VCO are powered using the microphone-bias from Pin 4. The host device performs demodulation and extracts the systolic BP, diastolic BP and mean arterial pressure (MAP) values. In another embodiment of the present disclosure a primary cell or a secondary cell (figure not shown) may be used in the smart accessory to power to the sensor, amplifier and the modulator.

In an example embodiment of the present disclosure, the sensor 404 as shown in FIG. 7A may be a thermopile, infra red (IR) sensor to sense temperature. The IR sensor incorporates thermopiles to detect temperature and a thermal resistor or thermistor that changes resistance based on the detected temperature. The IA 501 converts the resistance changes due to thermistor in to a voltage changes. The VCO 502, shown in FIG. 7A generates a frequency in the audio range corresponding to the temperature. The sensor 404 and the electronics 403 may be incorporated in small module with an ear probe and a jack for plugging in to a second device socket (figure not shown). The second device receives signal from sensor 404 up on connection and performs demodulation to estimate the temperature.

Figure 7B:
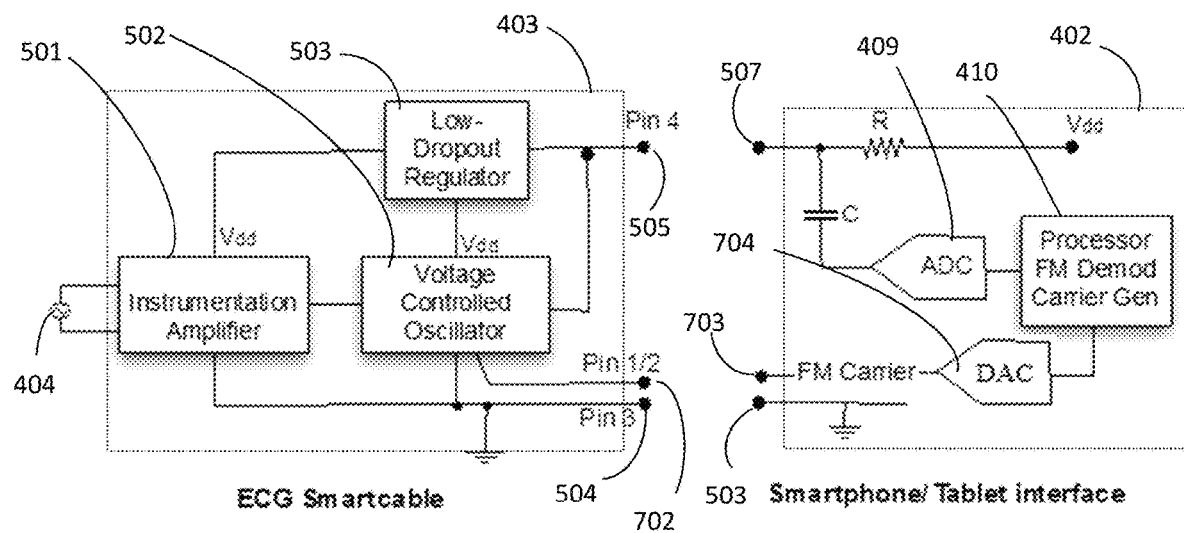
FIG. 7B shows a block diagram of an electronic module of the smart accessory, according to another embodiment of the present disclosure.

FIG. 7B shows an electronic module 403 of a first device configured to receive a carrier signal generated at a second device 402, for performing frequency modulation, in accordance with an embodiment of the present disclosure. The carrier frequency signal for the VCO 502 is generated using internal application on the processor and delivered to the first device on either Pin 1 (Audio Left) or Pin 2 (Audio Right) 702. This way of generating frequency carrier signal provides additional benefit of providing a stable reference during the demodulation process in the second device. In addition, this generation of frequency carrier signal reduces the cost and size of the electronics module 403 embedded in the first device, which is as shown in FIG. 7B.

Figure 7C:
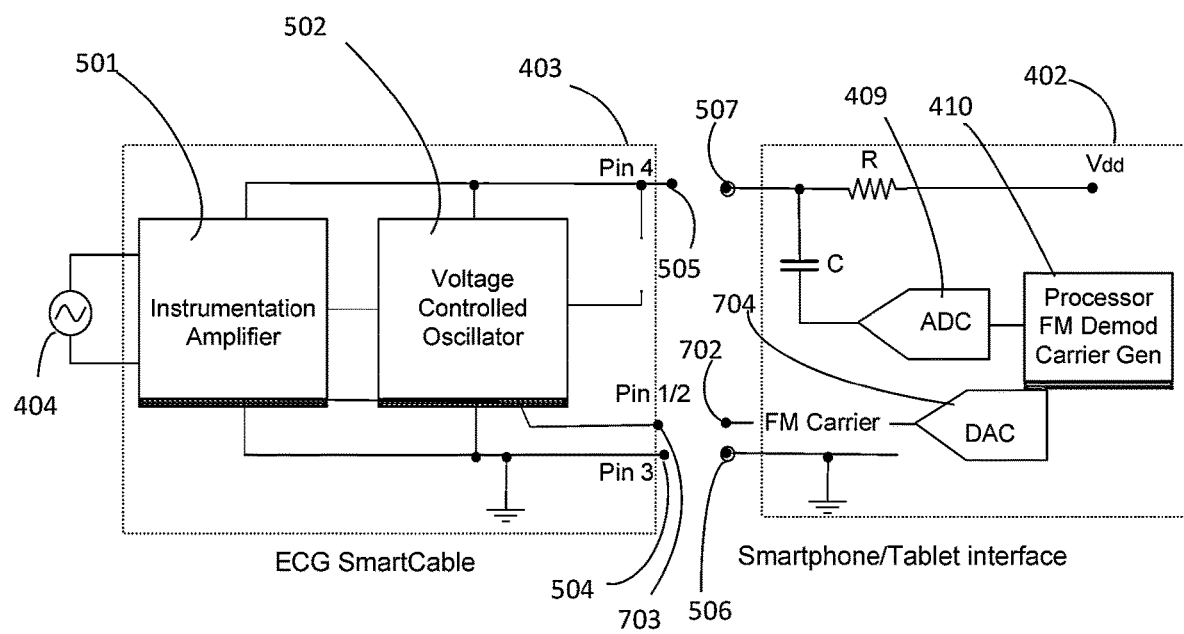
FIG. 7C shows a block diagram of an electronic module of the smart accessory without low-dropout regulator, according to yet another embodiment of the present disclosure.

In one embodiment, an electronic module of the first device or the smart accessory or the smartcable without use of low dropout regulator is shown in FIG. 7C. An instrumentation amplifier (IA) 501 receives signals from one or more sensors/transducers 404 through one or more cables of the first device. The sensors 404, 602, 803 may include, but not limited to ECG, EEG, airflow, temperature, light intensity, pressure and motion signals. The differential signal from two cables (or one ECG Lead), connected to two sensors/transducers is converted to a single-ended signal and amplified by the IA 501. The IA 501 and the VCO 502 are powered using the microphone-bias from a Pin 4 403. A capacitor (not shown in FIG. 5) may be placed in close proximity to the power supply pins of the IA 501 and the VCO 502 to improve Power Supply Rejection Ration (PSRR).

One embodiment of the present disclosure is a first device or a smartcable connected to a second device or a host device for measuring peripheral arterial oxygen saturation (SpO2). A pulse oximeter is used to measure arterial oxygen saturation in peripheral tissues. The pulse oximeter comprises a plurality of light emitting diodes (LED) and a photodetector. The photodetector converts received light from said LEDs to a corresponding voltage. The LEDs emit light at specific wavelengths when excited and elicit a response from the photodetector.

Figure 8:
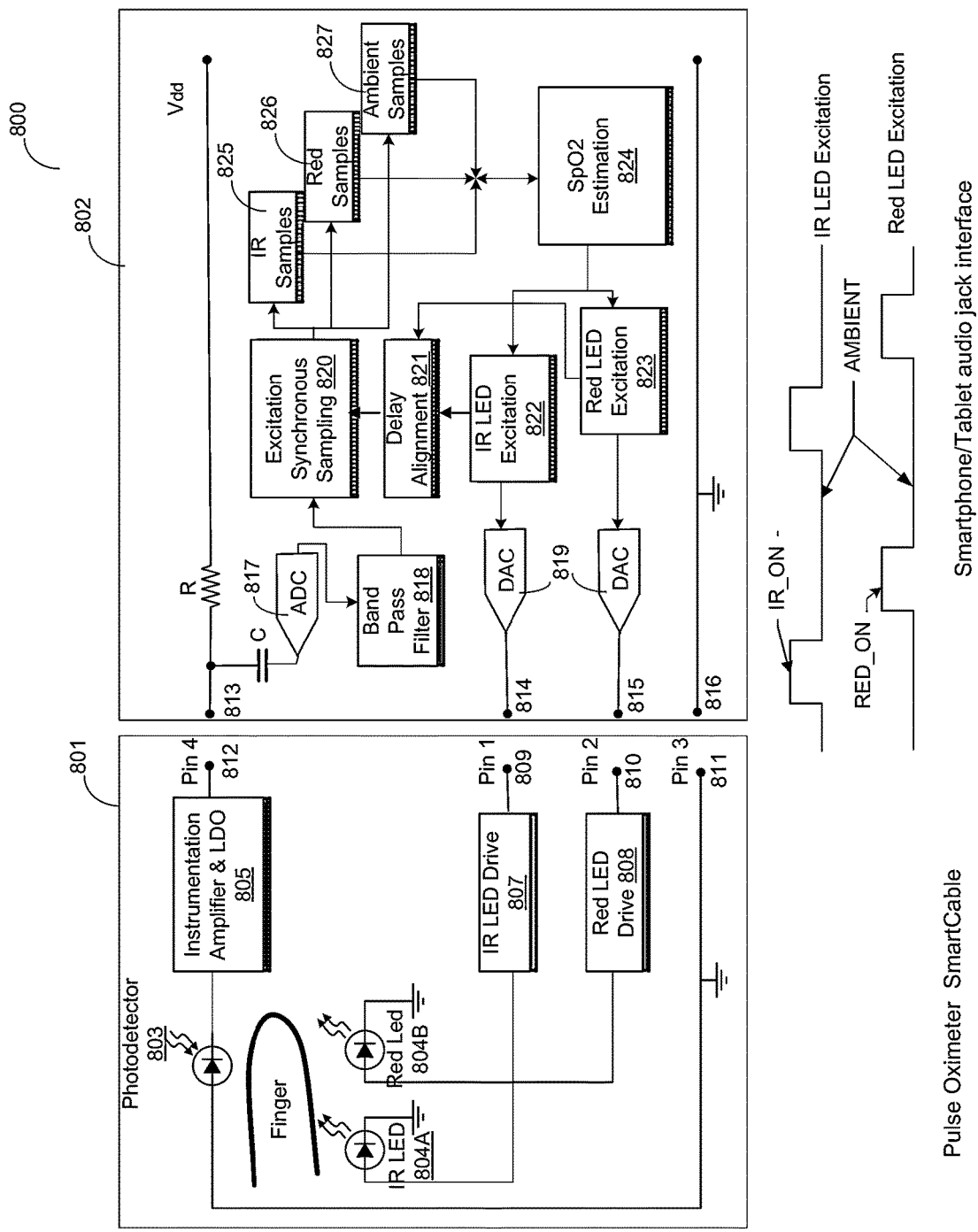
FIG. 8 shows an illustration of monitoring oxygen saturation using pulse oximeter smartcable, according to an embodiment of the present disclosure.

FIG. 8 shows an illustration of monitoring oxygen saturation using pulse oximeter according to an embodiment of the present disclosure. As shown in FIG. 8, when a light source via plurality of LEDs (804A and 804B, collectively referred as 804) and a photodetector 803 are placed on one of a finger, ear lobe or any other similar body part that is adequately perfused, the response of the photodetector depends on the pulsatile blood flow. The light source using a red LED drive 808 and an IR LD drive 807 illuminates the Red LED 804B and the Infra Red LED 804A respectively, in an alternating fashion to elicit response of the photodetector 803 to red and infrared light. A second device or a host device generates IR and Red LED excitation signals using an IR LED excitation block 822 and a red LED excitation block 823 respectively.

As shown in FIG. 8, the excitation of LEDs includes regions to enable photodetector 803 in sensing red light, IR light and ambient light. A low pass filtering effect is observed on the signals as they go through a digital to analog converter (DAC) 819 and analog interface through Pin 1 814, 809 and Pin 2 815, 810 to the IR LED drive 807 and red LED drive 808 respectively. The IR 807 and red LED drives 808 provide necessary bias and current to drive the LEDs 804. In one embodiment, the drives include diodes (not shown in the figure) to restore the square pulse shapes for accurate timing of actuating signals and capacitors to store adequate charge to elicit optimal response from the photodetector 803. Each of the LEDs 804 is driven around 16000 times a second, although other values are possible depending on the drive circuits used. As shown in FIG. 8, the instrumentation amplifier (IA) 805 receives power from Low dropout regulator (LDO) for performing signal conditioning.

In one embodiment a VCO may not be required, as the frequency of the information at Pin 4 is already in the audio band. At the second device or the host device, the digitised data is band pass filtered using a band pass filter 818 to eliminate noise. The filtered data is re-sampled in synchronization with excitation signals by the Excitation Synchronous Sampling module 820 to generate samples during red LED activation, IR LED activation and ambient conditions, which are received by IR samples unit 825, red samples unit 825 and ambient samples unit 827 respectively. In one embodiment, a delay alignment module 821 may compensate for any delays due to the latencies related to the audio interface, drive circuits, and the band pass filter (BPF). In one embodiment, the delay alignment module 821 may receive timing information from the IR LED Excitation module 822 and the Red LED Excitation module 823.

FIG. 9 shows a first device or a smartcable with multiple sensors, in accordance with an embodiment of the present disclosure. FIG. 9 shows two ECG signals 404A, 404B as an example. The audio bandwidth supported by a headset socket and an analog to digital converter (ADC) of a second device is much greater than that required for frequency modulated ECG, even with the large FM bandwidth of 5-6 kHz. This allows the first device to support more than one ECG lead with proper allocation of channels and using Frequency Division Multiple Access (FDMA). As an example, the first device may support a 3-Lead ECG by using two instrumentation amplifiers 501A, 501B, two modulators or voltage controlled oscillators and a summer or an adder 901 using an op-amp, as shown in FIG. 9. The second device processor 410 implements multiple band pass filters to separate channels and demodulate each ECG channel.

As shown in FIG. 9, for the first device or the smartcable it is possible to acquire plurality of limb leads (I, II and III) using two FM channels, since any two limb leads can be combined to derive the third lead as shown below:

Lead I=LA−RA=Lead II−Lead III

Lead II=LL−RA=Lead III+Lead I

Lead III=LL−LA=Lead II−Lead I

Also, the embodiment as shown in FIG. 9 may monitor fetal ECG, along with mother's ECG. The two electrodes for fetal ECG will use a waistband, instead of two wrist/ankle fasteners. This is not shown in FIG. 9, but one skilled in the art will readily recognize that multiple sensors, including but not limited to ECG, EEG, motion, airflow, temperature, light intensity, pressure and other physiological signals can be sensed by a plurality of IA and VCO modules in the first device and communicated to the second device or Host device as a composite analog signal. The ADC 409 in the Host device receives the composite signal, with plurality of signals frequency modulated at different center frequencies. The ADC 409 converts this analog data in to composite discrete FM stream, comprising one or more of ECG, EEG, motion, airflow, body temperature, light intensity changes due to arterial oxygen saturation level, blood pressure and other physiological signals.

FIG. 10 shows a block diagram of a second device or a host device, in accordance with an embodiment of the present disclosure. The second device comprises of at least one analog to digital convertor (ADC) 409, at least one processor 410, at least one display unit 1002, at least one user input unit 1001, memory or storage unit 1002 and at least one modem 411. The ADC 409 of the second devices such as, but not limited to, smartphones, tablets, personal computers, PDAs and any other computing device provide 48, 96, or 192 kHz sampling with 24 bits/sample resolution. The audio bandwidth commonly used is in the range of is 50 Hz to 18 kHz. As shown in FIG. 1, the AC coupling due to capacitor C does not affect audio performance, as there is negligible information in frequencies below 50 Hz. Consequently, the AC coupling in the second device will not affect the performance of the first device or smartcable, since the center frequencies of VCOs for all the sensors are chosen to be much higher than 50 Hz. Human auditory system has up to 120 dB dynamic range and most consumer audio solutions have 90+dB dynamic range. This is supported by 24 bits/sample in many Host devices. The dynamic range provided by 24 bits/sample is more than adequate for digitizing the composite FM signal from the smartcable.

Figure 11:
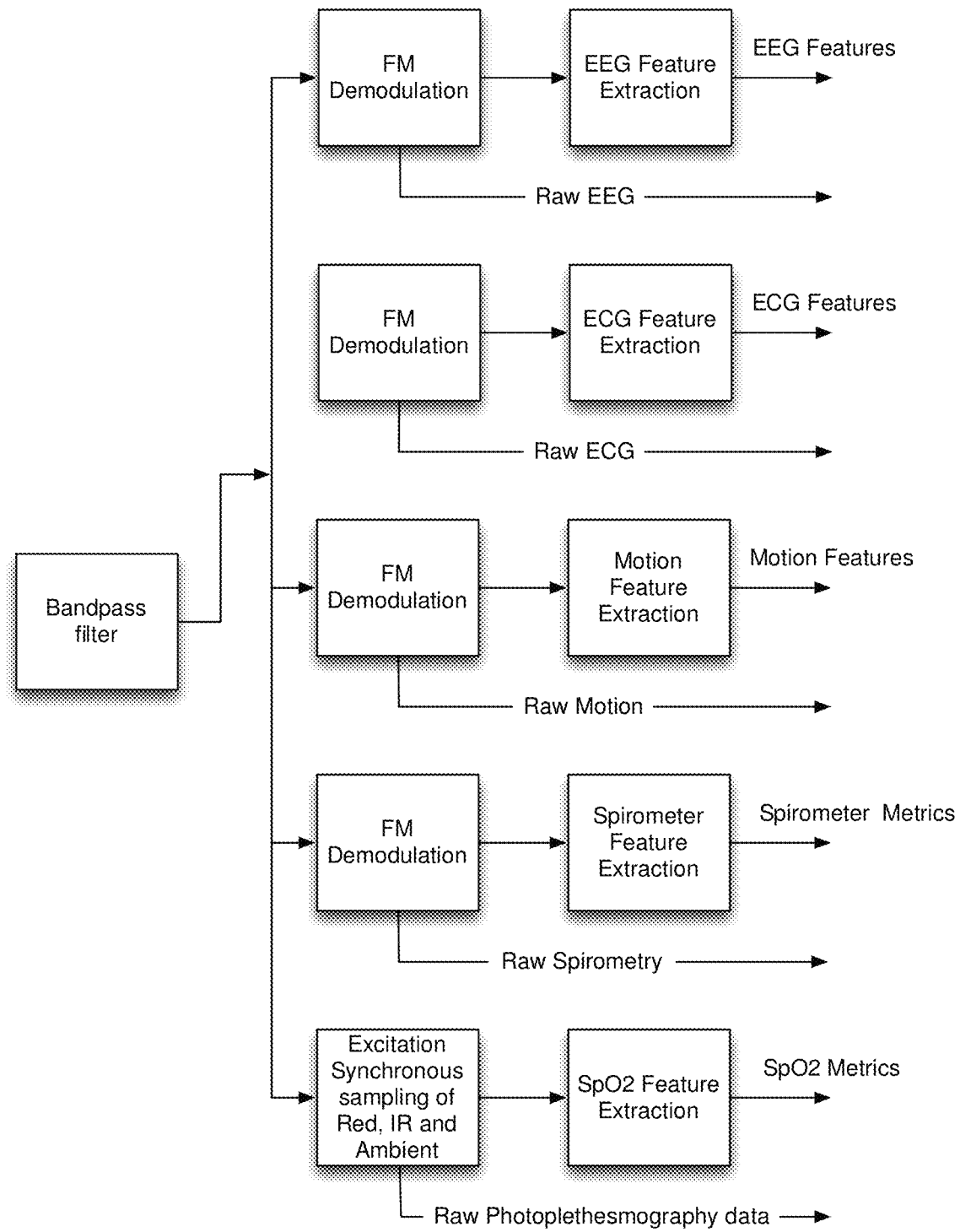
FIG. 11 shows a Signal and Feature extraction Module of the host side for ECG, EEG, motion, airflow, temperature, light intensity, pressure and other signals, in accordance with an embodiment of the present disclosure.

FIG. 11 shows a signal processing module of the second device side, in accordance with an embodiment of the present disclosure. The signal processing module comprises a bandpass filter, one or more FM demodulation blocks and one or more feature extraction blocks. The bandpass filter performs band-pass filtering of the composite FM signal to extract one or more FM streams. A Finite Impulse Response (FIR) filter has phase linearity properties and is ideal to perform the bandpass filtering of single sensor information. The bandpass filter effectively separates each FM modulated signal from the composite discrete signal received from the ADC. The FM demodulation module translates each discrete sensor stream to a base band stream. The FM demodulation is performed using the techniques such as, but not limited to Hilbert Filter approach, Phase Locked Loop, and other FM demodulation techniques. The processing module then extracts signal features such as, but not limited to ECG fiduciary points (PQRST), average heart rate (HR), instantaneous heart rate (IHR), and pNN50 or heart rate variability; EEG features, motion features corresponding to physical activity; spirometer features corresponding to pulmonary function, SpO2 for oxygen saturation, blood pressure features, body temperature, etc.

One embodiment of the present disclosure is a Display and Storage Module, in accordance with an embodiment of the present disclosure. The Display and Storage Module control the display unit and storage of data for post-processing and communication. The display unit provides at least one of user input unit and Graphical User Interface (GUI) with a touch screen interface on host device, as shown in FIG. 10. The host device provides user input unit to configure smart accessories and receive signals from smart accessories. The GUI also provides for touch screen and mouse control for manipulating the display of raw signals and extracted features on host device such as, but not limited to, smartphones, tablets, Laptops and personal devices. The storage unit stores the sensor signals and processed data for post processing, including comparison with previous recordings for trend analysis, comparison with cohorts for statistical analysis, etc.

In one embodiment of the present disclosure, the communication module transmits the sensor raw signals and the extracted features to a third device such as another computer or a database server in the Internet. The communication module may also perform additional functions such as posting appropriate data to Electronic Medical Records (EMR) and/or sending alerts to the second device when certain signal features exceed pre-programmed thresholds.

One embodiment of the present disclosure is a third device comprising at least one control unit, at least one modem, and at least one Graphical User Interface unit. The at least one control unit is configured to receive at least one composite digital signal and perform at least one of band pass filtering, demodulation and extracting at least one raw signal sensed by a first device. The third device further comprises one or more band pass filters to perform band pass filtering. In one embodiment, each of the one or more band pass filters may have equal bandwidths. In another embodiment, the at least one of the one or more band pass filters have a different bandwidth compared to at least one another band pass filter.

The at least one control unit of the third device is configured to receive one or more threshold values and compare the extracted one or more extracted features of the at least one raw signal against the one or more threshold values. The demodulation performed by the at least one control unit is one of frequency demodulation, amplitude demodulation and phase demodulation. The at least one Graphical User Interface unit of the third device is configured to receive one or more input commands and display information associated with the demodulation.

In one embodiment, the third device is configured to generate an alarm when the at least one extracted feature is greater than an upper threshold value or less than a lower threshold value, wherein the upper and the lower threshold values are associated with at least one of electrocardiogram (ECG), Electroencephalography (EEG), motion, airflow of respiratory system, body temperature, arterial oxygen saturation level, blood pressure and any other physiology signal.

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

As used herein, a phrase referring to "at least one of" a list of items refers to any combination of those items, including single members. As an example, "at least one of: a, b, or c" is intended to cover: a, b, c, a-b, a-c, b-c, and a-b-c.

The various illustrative logical blocks, modules and circuits described in connection with the present disclosure may be implemented or performed with a general purpose processor, a digital signal processor (DSP), an application specific integrated circuit (ASIC), a field programmable gate array signal (FPGA) or other programmable logic device (PLD), discrete gate or transistor logic, discrete hardware components including operational amplifiers, instrumentation amplifiers or any combination thereof designed to perform the functions described herein. A general purpose processor may be a microprocessor, but in the alternative, the processor may be any commercially available processor, controller, microcontroller or state machine. A processor may also be implemented as a combination of computing devices, e.g., a combination of a DSP and a microprocessor, a plurality of microprocessors, one or more microprocessors in conjunction with a DSP core, or any other such configuration.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

The functions described may be implemented in hardware, software, firmware, or any combination thereof. If implemented in software, the functions may be stored or transmitted over as one or more instructions or code on a computer-readable medium. Computer-readable media include both computer storage media and communication media including any medium that facilitates transfer of a computer program from one place to another. A storage medium may be any available medium that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared (IR), radio, and microwave, then the coaxial cable, fiber optic cable, twisted pair, DSL, or wireless technologies such as infrared, radio, and microwave are included in the definition of medium. Disk and disc, as used herein, include compact disc (CD), laser disc, optical disc, digital versatile disc (DVD), floppy disk, and Bluray disc where disks usually reproduce data magnetically, while discs reproduce data optically with lasers. Thus, in some aspects computer-readable media may comprise non-transitory computer-readable media (e.g., tangible media). In addition, for other aspects computer-readable media may comprise transitory computer-readable media (e.g., a signal). Combinations of the above should also be included within the scope of computer-readable media.

Thus, certain aspects may comprise a computer program product for performing the operations presented herein. For example, such a computer program product may comprise a computer readable medium having instructions stored (and/or encoded) thereon, the instructions being executable by one or more processors to perform the operations described herein. For certain aspects, the computer program product may include packaging material.

Software or instructions may also be transmitted over a transmission medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of transmission medium.

Further, it should be appreciated that modules and/or other appropriate means for performing the methods and techniques described herein can be downloaded and/or otherwise obtained by a user terminal and/or base station as applicable. For example, such a device can be coupled to a server to facilitate the transfer of means for performing the methods described herein. Alternatively, various methods described herein can be provided via storage means (e.g., RAM, ROM, a physical storage medium such as a compact disc (CD) or floppy disk, USB storage devices, etc.), such that a user terminal and/or base station can obtain the various methods upon coupling or providing the storage means to the device. Moreover, any other suitable technique for providing the methods and techniques described herein to a device can be utilized.

It is to be understood that the claims are not limited to the precise configuration and components illustrated above. Various modifications, changes and variations may be made in the arrangement, operation and details of the methods and apparatus described above without departing from the scope of the claims.

The teachings herein may be incorporated into (e.g., implemented within or performed by) a variety of apparatuses (e.g., devices). For example, one or more aspects taught herein may be incorporated into a phone (e.g., a cellular phone), a personal data assistant ("PDA"), a smartphone, an entertainment device (e.g., a portable media device, including music and video players), a headset (e.g., headphones, an earpiece, etc.), a microphone, a medical sensing device (e.g., a biometric sensor, a heart rate monitor, a pedometer, an ECG device, a smart bandage, etc.), a user I/O device (e.g., a watch, a remote control, a light switch, a keyboard, a mouse, etc.), an environment sensing device (e.g., a tire pressure monitor), a monitoring device that may receive data from the medical or environment sensing device (e.g., a desktop, a mobile computer, etc.), a point-of-care device, a hearing aid, a set-top box, or any other suitable device. The monitoring device may also have access to data from different sensing devices via connection with a network.

In some aspects a wireless device may comprise an access device (e.g., an access point) for a communication system. Such an access device may provide, for example, connectivity to another network (e.g., a wide area network such as the Internet or a cellular network) via a wired or wireless communication link. Accordingly, the access device may enable another device (e.g., a wireless station) to access the other network or some other functionality. In addition, it should be appreciated that one or both of the devices may be portable or, in some cases, relatively non-portable. Also, it should be appreciated that a wireless device also may be capable of transmitting and/or receiving information in a non-wireless manner (e.g., via a wired connection) via an appropriate communication interface.

The specification has described a method and a system for providing real time remote guidance by an expert to a novice user to accomplish a task. The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

It is intended that the disclosure and examples be considered as exemplary only, with a true scope and spirit of disclosed embodiments being indicated by the following claims.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and devices within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

In addition, where features or aspects of the disclosure are described in terms of Markush groups, those skilled in the art will recognize that the disclosure is also thereby described in terms of any individual member or subgroup of members of the Markush group.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

I claim:

1. A second device comprising:
a) at least one ADC being configured to receive a composite analog signal from a first device, the composite analog signal comprising a plurality of frequency modulated signals, each signal in the frequency modulated signals being frequency modulated to a distinct center frequency, each signal in the frequency modulated signals originating from a sensor, at least two of the signals in the frequency modulated signals comprising a plurality of frequency components, the at least one ADC being configured to convert the frequency modulated signals into a digital signal; and
b) at least one control unit configured to receive the digital signal and perform: band pass filtering, frequency demodulation, and extraction of the signals sensed by the sensors.

2. The second device according to claim 1, wherein the signals in the frequency modulated signals comprise a plurality of at least one of the following signals:
a) electrocardiogram (ECG);
b) Electroencephalography (EEG);
c) motion;
d) respiratory system airflow;
e) body temperature;
f) light intensity changes caused by arterial oxygen saturation level; or
g) blood pressure.

3. The second device according to claim 1, further comprising a plurality of band pass filters configured to perform the band pass filtering, each of the band pass filters configured with equal bandwidths.

4. The second device according to claim 1, further comprising a plurality of band pass filters configured to perform the band pass filtering, at least two of the band pass filters having distinct bandwidths.

5. The second device according to claim 1, further comprising at least one display interface unit configured to display information associated with the signals in the frequency modulated signals.

6. The second device according to claim 1, further comprising at least one display interface unit configured to display at least one feature extracted from one of the signals in the frequency modulated signals.

7. The second device according to claim 1, further comprising at least one modem configured to transmit information associated with at least one of the signals in the frequency modulated signals to another device.

8. The second device according to claim 1, further comprising at least one modem configured to transmit at least one feature extracted from one of the signals in the frequency modulated signals to another device.

9. The second device according to claim 1, further comprising at least one modem configured to transmit at least one sample of one of the signals in the frequency modulated signals to another device.

10. The second device according to claim 1, wherein the control unit is further configured to compare at least one feature extracted from one of the signals in the frequency modulated signals against a threshold value.

11. A method comprising:
   a) receiving a composite analog signal, the composite analog signal comprising a plurality of frequency modulated signals, each signal in the frequency modulated signals being frequency modulated to a distinct center frequency, each signal in the frequency modulated signals originating from a sensor, at least two of the signals comprising a plurality of frequency components;
   b) converting the frequency modulated signals into a digital signal through employment of at least one ADC;
   c) performing band pass filtering and frequency demodulation on the digital signal; and
   d) extracting the signals sensed by the sensors.

12. The method according to claim 11, wherein the signals in the frequency modulated signals comprise a plurality of at least one of the following signals:
   a) electrocardiogram (ECG);
   b) Electroencephalography (EEG);
   c) motion;
   d) respiratory system airflow;
   e) body temperature;
   f) light intensity changes caused by arterial oxygen saturation level; or
   g) blood pressure.

13. The method according to claim 11, wherein the band pass filtering is performed through employment of a plurality of band pass filters configured with equal bandwidths.

14. The method according to claim 11, wherein the band pass filtering is performed through employment of a plurality of band pass filters, at least two of the band pass filters having distinct bandwidths.

15. The method according to claim 11, further comprising displaying information associated with the signals in the frequency modulated signals.

16. The method according to claim 11, further comprising displaying at least one feature extracted from one of the signals in the frequency modulated signals.

17. The method according to claim 11, further comprising transmitting information associated with at least one of the signals in the frequency modulated signals to another device.

18. The method according to claim 11, further comprising transmitting at least one feature extracted from one of the signals in the frequency modulated signals to another device.

19. The method according to claim 11, further comprising transmitting at least one sample of one of the signals in the frequency modulated signals to another device.

20. The method according to claim 11, further comprising comparing at least one feature extracted from one of the signals in the frequency modulated signals against a threshold value.

* * * * *